(12) United States Patent
Nageri et al.

(10) Patent No.: US 10,543,374 B2
(45) Date of Patent: Jan. 28, 2020

(54) CONNECTOR ASSEMBLIES WITH BENDING LIMITERS FOR ELECTRICAL STIMULATION SYSTEMS AND METHODS OF MAKING AND USING SAME

(71) Applicant: Boston Scientific Neuromodulation Corporation, Valencia, CA (US)

(72) Inventors: Ranjan Krishna Mukhari Nageri, Valencia, CA (US); Geoffrey Abellana Villarta, Valencia, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 43 days.

(21) Appl. No.: 15/715,974

(22) Filed: Sep. 26, 2017

(65) Prior Publication Data

US 2018/0093098 A1 Apr. 5, 2018

Related U.S. Application Data

(60) Provisional application No. 62/402,715, filed on Sep. 30, 2016.

(51) Int. Cl.
*A61N 1/375* (2006.01)
*A61N 1/05* (2006.01)
(Continued)

(52) U.S. Cl.
CPC .............. *A61N 1/3752* (2013.01); *A61N 1/05* (2013.01); *A61N 1/0551* (2013.01);
(Continued)

(58) Field of Classification Search
CPC ........ H01R 24/58; H01R 13/15; H01R 13/44; H01R 13/03; A61N 1/3752; A61N 1/05; A61N 1/0551; A61N 1/3605
(Continued)

(56) References Cited

U.S. PATENT DOCUMENTS 3,222,471 A  12/1965  Steinkamp
3,601,747 A  8/1971  Prall et al.
(Continued)

FOREIGN PATENT DOCUMENTS

EP  0580928 A1  2/1994
EP  0650694 B1  7/1998
(Continued)

*Primary Examiner* — Edwin A. Leon
*Assistant Examiner* — Milagros Jeancharles
(74) *Attorney, Agent, or Firm* — Lowe Graham Jones PLLC; Bruce E. Black

(57) ABSTRACT

A connector assembly includes an elongated connector housing defining a port at the second end of the connector housing for receiving a proximal end of a lead or lead extension; a lumen that extends from the port along at least a portion of the length of the connector housing; connector contacts axially spaced-apart and disposed along the lumen; and non-conductive spacers disposed between adjacent connector contacts, at least one of the non-conductive spacers includes a first region. One or more additional features are included to resist bending of the connector assembly. One such feature is a non-conductive first insert disposed between adjacent connector contacts to maintains a minimum distance between the adjacent connector contacts. Another feature is a stiffening element disposed within apertures in the spacers and connecting two or more of the spacers. Yet another feature is a stiffening sleeve disposed within the housing.

20 Claims, 10 Drawing Sheets

(51) Int. Cl.
*A61N 1/36* (2006.01)
*H01R 24/58* (2011.01)
*H01R 13/15* (2006.01)

(52) U.S. Cl.
CPC ........... *A61N 1/3605* (2013.01); *H01R 24/58* (2013.01); *H01R 13/15* (2013.01)

(58) Field of Classification Search
USPC ........................................ 439/752, 668, 669
See application file for complete search history.

(56) References Cited

U.S. PATENT DOCUMENTS

| | | |
|---|---|---|
| 3,718,142 A | 2/1973 | Mulier |
| 3,757,789 A | 9/1973 | Shenker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffmann et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,138 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,143 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,957,968 A * | 9/1999 | Belden .................. A61N 1/057 |
| | | 604/175 |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezal |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |

(56) References Cited

U.S. PATENT DOCUMENTS

| | | | |
|---|---|---|---|
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 4/2009 | Marvin et al. |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,654,843 B2 * | 2/2010 | Olson ............... A61N 1/3752 |
| | | 439/248 |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 * | 3/2014 | DeRohan ............ A61N 1/0551 |
| | | 607/38 |
| 8,688,235 B1 | 4/2014 | Pianca et al. |
| 8,738,138 B2 * | 5/2014 | Funderburk ......... A61N 1/3752 |
| | | 607/45 |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,162,055 B2 * | 10/2015 | Pianca ................ A61N 1/0553 |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,492,666 B2 * | 11/2016 | Smith ................ A61N 1/3752 |
| 9,498,618 B2 | 11/2016 | Stetson et al. |
| 9,498,820 B2 | 11/2016 | Romero et al. |
| 9,504,839 B2 | 11/2016 | Leven |
| 9,604,068 B2 | 3/2017 | Malinowski |

(56) References Cited

U.S. PATENT DOCUMENTS

| | | |
|---|---|---|
| 9,656,093 B2 | 5/2017 | Villarta et al. |
| 9,770,598 B2 | 9/2017 | Malinowski et al. |
| 9,775,988 B2 * | 10/2017 | Govea ............... A61N 1/0534 |
| 9,782,582 B2 * | 10/2017 | Govea ............... A61N 1/08 |
| 9,839,787 B2 * | 12/2017 | Villarta ............... A61N 1/3752 |
| 9,855,413 B2 * | 1/2018 | Vadlamudi ............ A61N 1/05 |
| 9,878,148 B2 * | 1/2018 | Leven ................ A61N 1/0551 |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 * | 8/2003 | Kast ................ A61N 1/3752 607/36 |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 * | 9/2007 | Honour ............... A61B 5/0422 606/41 |
| 2007/0225772 A1 * | 9/2007 | Lahti ................ A61N 1/3752 607/37 |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 * | 8/2008 | Janzig ................ A61N 1/3752 607/37 |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 * | 1/2011 | Brase ................ A61N 1/3752 607/2 |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184479 A1 * | 7/2011 | Kast ................ A61N 1/3752 607/2 |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 * | 11/2011 | Janzig ................ H01R 13/187 607/2 |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 * | 3/2012 | Sundaramurthy ... A61N 1/3752 607/2 |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 * | 8/2012 | DiGiore ............... A61N 1/0534 607/148 |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0213118 A1 * | 7/2014 | Glynn ................ A61N 1/3752 439/675 |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0018916 A1 * | 1/2015 | Leven ................ A61N 1/0553 607/116 |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |

(56) References Cited

U.S. PATENT DOCUMENTS

| | | |
|---|---|---|
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1 | 10/2016 | Govea et al. |
| 2016/0375238 A1 | 12/2016 | Leven et al. |
| 2017/0014635 A1* | 1/2017 | Villarta ............... A61N 1/3752 |
| 2017/0072187 A1* | 3/2017 | Howard ................ A61N 1/05 |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

* cited by examiner

CONNECTOR ASSEMBLIES WITH BENDING LIMITERS FOR ELECTRICAL STIMULATION SYSTEMS AND METHODS OF MAKING AND USING SAME

CROSS-REFERENCE TO RELATED APPLICATIONS

This application claims the benefit under 35 U.S.C. § 119(e) of U.S. Provisional Patent Application Ser. No. 62/402,715, filed Sep. 30, 2016, which is incorporated herein by reference.

FIELD

The present invention is directed to the area of implantable electrical stimulation systems and methods of making and using the systems. The present invention is also directed to implantable neuromodulation lead extensions with stiffened connector assemblies, as well as methods of making and using the same.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a connector assembly including an elongated connector housing having a first end, a second end, and a length, the connector housing defining a port at the second end of the connector housing, the port configured for receiving a proximal end of a lead or lead extension; a lumen that extends from the port along at least a portion of the length of the connector housing; connector contacts axially spaced-apart and disposed along the lumen such that the connector contacts are each exposed to the lumen, the connector contacts configured for coupling to a proximal end of a lead or lead extension when the proximal end of the lead or lead extension is inserted into the lumen; non-conductive spacers disposed between adjacent connector contacts, at least one of the non-conductive spacers includes a first region, wherein during bending of the connector assembly in a first plane the first region is placed under a compressive stress; and at least one non-conductive first insert disposed on or within the first region between adjacent connector contacts, the at least one first insert having a length that maintains a minimum distance between the adjacent connector contacts when the first region is placed under the compressive stress.

In at least some embodiments, the spacers are made from a first material and the at least one first insert is made from a second material that is stiffer than the first material. In at least some embodiments, each of the non-conductive spacers includes the first region, and the at least one non-conductive first insert includes a plurality of non-conductive first inserts with one of the first inserts disposed in each first region. In at least some embodiments, the connector assembly further includes a plurality of second inserts with a one of the second inserts disposed on or within each of the plurality of non-conductive spacers, the second inserts longitudinally aligned and circumferentially offset with respect to the first inserts.

In at least some embodiments, the connector assembly further includes at least one non-conductive second insert disposed on or within at least one of the plurality of non-conductive spacers, wherein the at least one second insert is circumferentially offset with respect to the at least one first insert disposed on or within the first region. In at least some embodiments, the connector assembly further includes at least one third and at least one fourth insert disposed on or within at least one of the plurality of non-conductive spacers, wherein the at least one first insert disposed on or within the first region and the second, third and fourth inserts are circumferentially and equidistantly spaced apart with respect to each other. In at least some embodiments, the connector assembly further includes bending of the connector assembly in a plane different from the first plane causes at least one of the second, third or fourth non-conductive inserts to maintain at least a minimum distance between adjacent connector contacts.

In at least some embodiments, the connector assembly further includes the at least one first insert is disposed, at least partially, by a recess formed in a one of the spacers. In at least some embodiments, the connector assembly further includes the elongated connector housing is disposed over the connector contacts, the spacers and the inserts.

Another embodiments is a connector assembly including an elongated connector housing having a first end, a second end, and a length, the connector housing defining a port at the second end of the connector housing, the port configured for receiving a proximal end of a lead or lead extension; a lumen that extends from the port along at least a portion of the length of the connector housing; connector contacts having an outer radius and axially spaced-apart and disposed along the lumen such that the connector contacts are each exposed to the lumen, the connector contacts configured for coupling to a proximal end of a lead or lead extension when the proximal end of the lead or lead extension is inserted into the lumen; non-conductive spacers disposed within spaces provided between adjacent connector contacts, each of the plurality of non-conductive spacers defining an aperture at a radius greater than the outer radius of the connector contacts; and a first stiffening element disposed within a plurality of the apertures and connecting at least two of the spacers, the first stiffening element configured and arranged to resist bending of connector assembly.

In at least some embodiments, the first stiffening element is more rigid than the spacers. In at least some embodiments, each of the plurality of non-conductive spacers includes a plurality of the apertures that are circumferentially and equidistantly spaced apart with respect to each other. In at least some embodiments, the connector assembly further includes at least one additional stiffening element, wherein the first stiffening element and the at least one additional stiffening element are disposed within different ones of the plurality of apertures and each connect at least two of the spacers. In at least some embodiments, the connector assembly further includes a sleeve disposed over the plurality of non-conductive spacers.

A further embodiment is a connector assembly including an elongated connector housing having a first end, a second end, and a length, the connector housing defining a port at the second end of the connector housing, the port configured for receiving a proximal end of a lead or lead extension; a lumen that extends from the port along at least a portion of the length of the connector housing; connector contacts axially spaced-apart and disposed along the lumen such that the connector contacts are each exposed to the lumen, the connector contacts configured for coupling to a proximal end of a lead or lead extension when the proximal end of the lead or lead extension is inserted into the lumen; non-conductive spacers disposed within spaces provided between adjacent connector contacts; and a stiffening sleeve disposed over the non-conductive spacers and connector contacts and disposed within the housing, wherein the sleeve is configured and arranged to resist bending of the connector assembly.

In at least some embodiments, the stiffening sleeve is more rigid than the plurality of non-conductive spacers. In at least some embodiments, the stiffening sleeve is a mesh sleeve. In at least some embodiments, the stiffening sleeve is shrink fit over the plurality of non-conductive spacers.

Yet another embodiment is a lead assembly including a lead; and a lead extension that contains any of the connector assemblies described above, the lead extension having a proximal end and a distal end, wherein the proximal end of the lead extension includes a plurality of terminals electrically insulated from one another.

Another embodiment is an electrical stimulating system including the lead assembly described above; and a control module coupleable to the lead assembly, the control module including a housing, and an electronic subassembly disposed in the housing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed implantable neuromodulation lead extensions and stiffened connector assemblies that may limit bending movement of components within the connector assemblies and mitigate against a misalignment or a decoupling of electrical connections within the connector assemblies, as well as methods of making and using the same.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/

0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Examples of connectors, connector contacts and connector assemblies for electrical stimulation systems with leads are found in, for example, U.S. Pat. Nos. 8,849,396; 7,244,150; 8,600,507; 8,897,876; 8,682,439; U.S. Patent Applications Publication Nos. 2012/0053646; 2014/0148885; 2015/0209575; 2016/0059019; and U.S. Patent Provisional Patent Application Nos. 62/193,472; 62/216,594; 62/259,463; and 62/278,667, all of which are incorporated by reference in their entireties.

Figure 1:
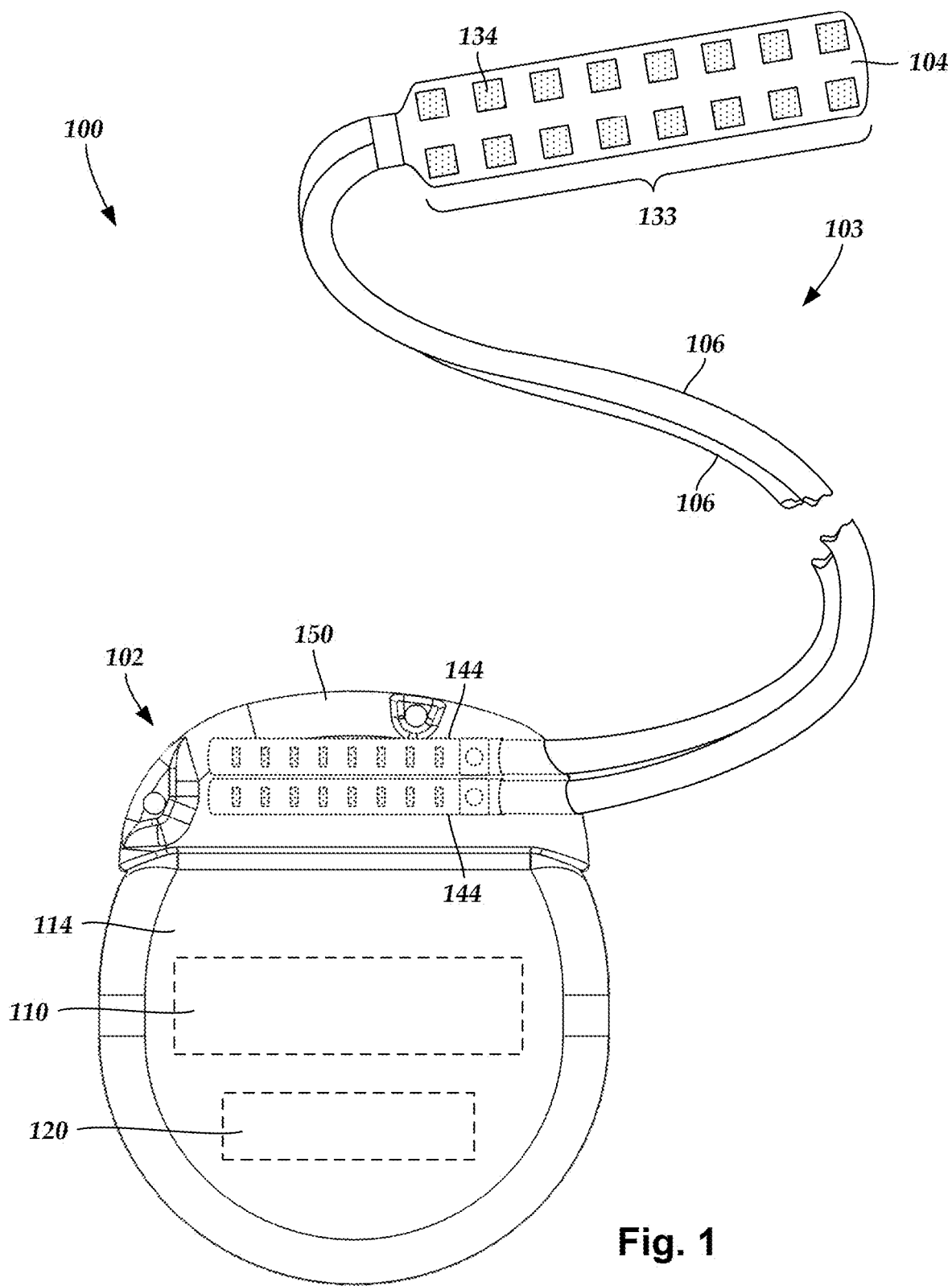
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
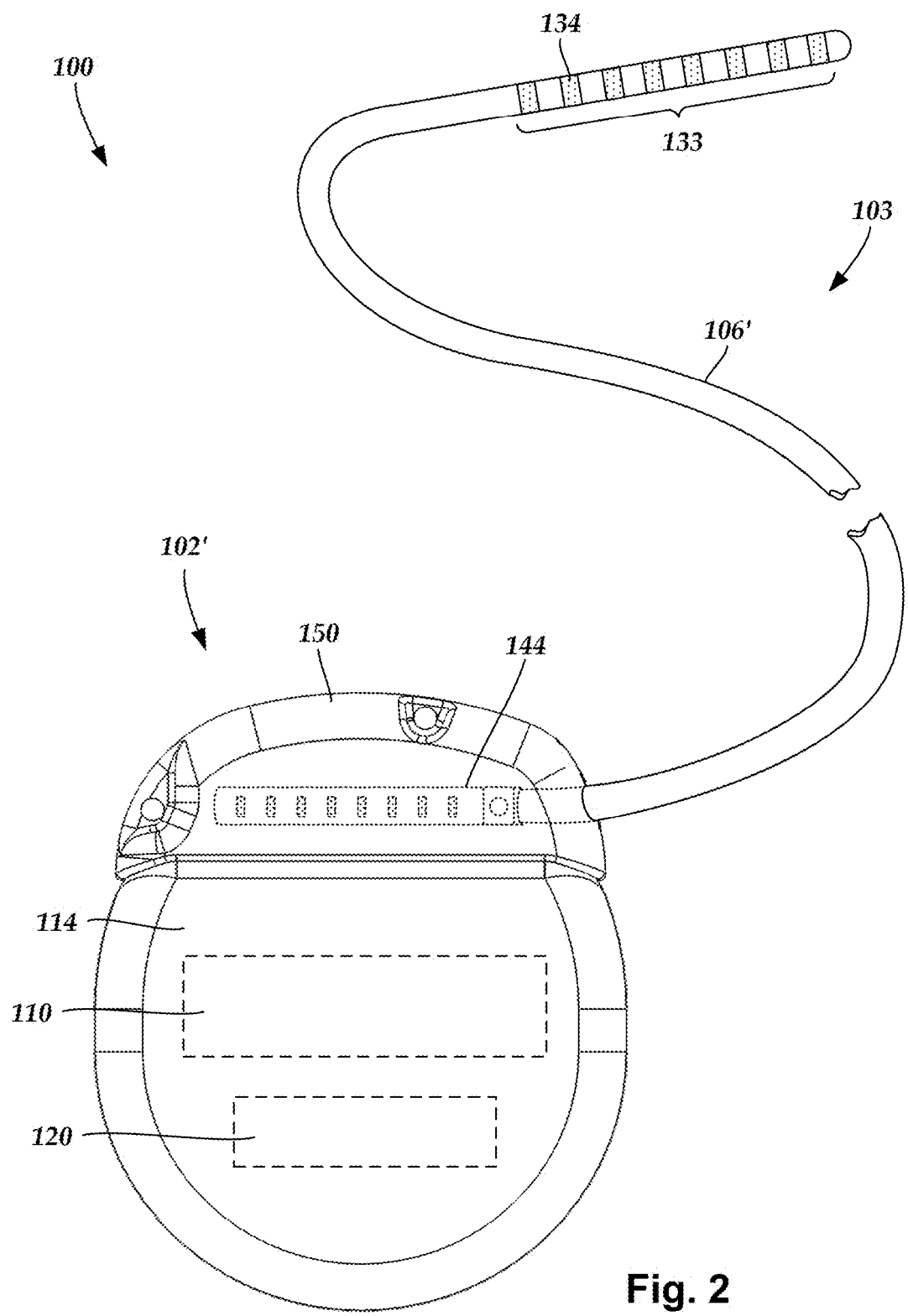
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
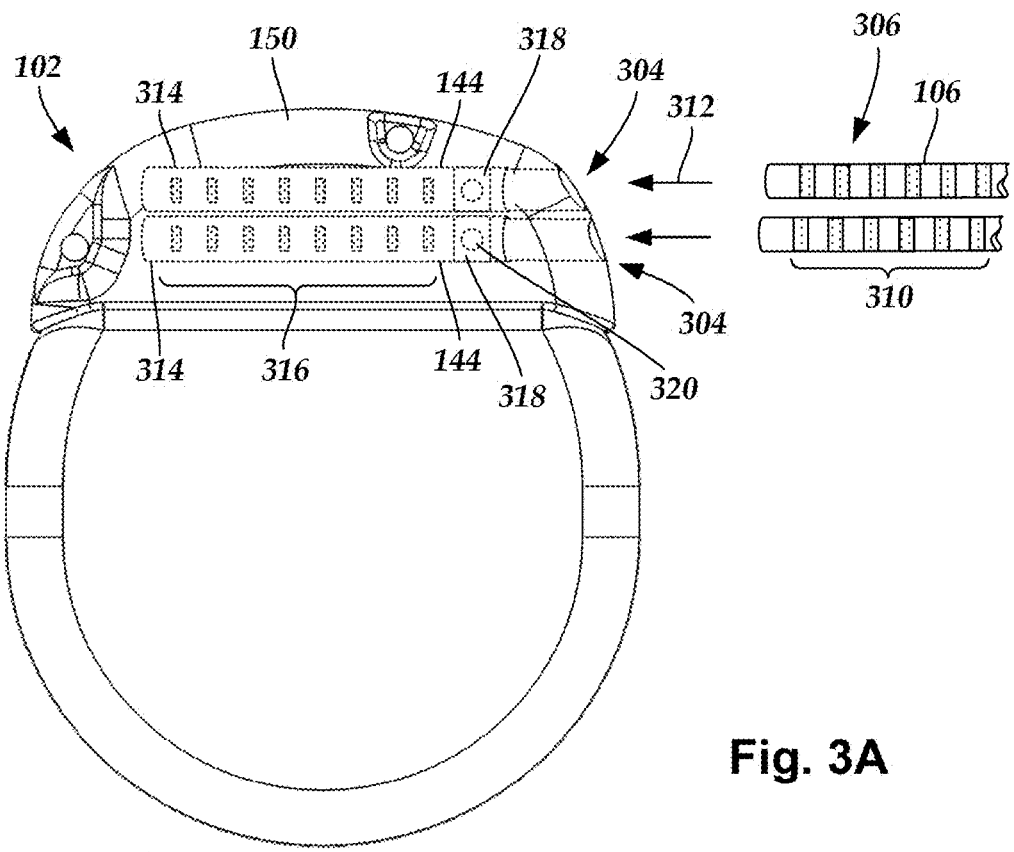
FIG. 3A is a schematic view of one embodiment of a plurality of connector assemblies disposed in the control module of FIG. 1, the connector assemblies configured to receive the proximal portions of the lead bodies of FIG. 1, according to the invention.
Figure 3B:
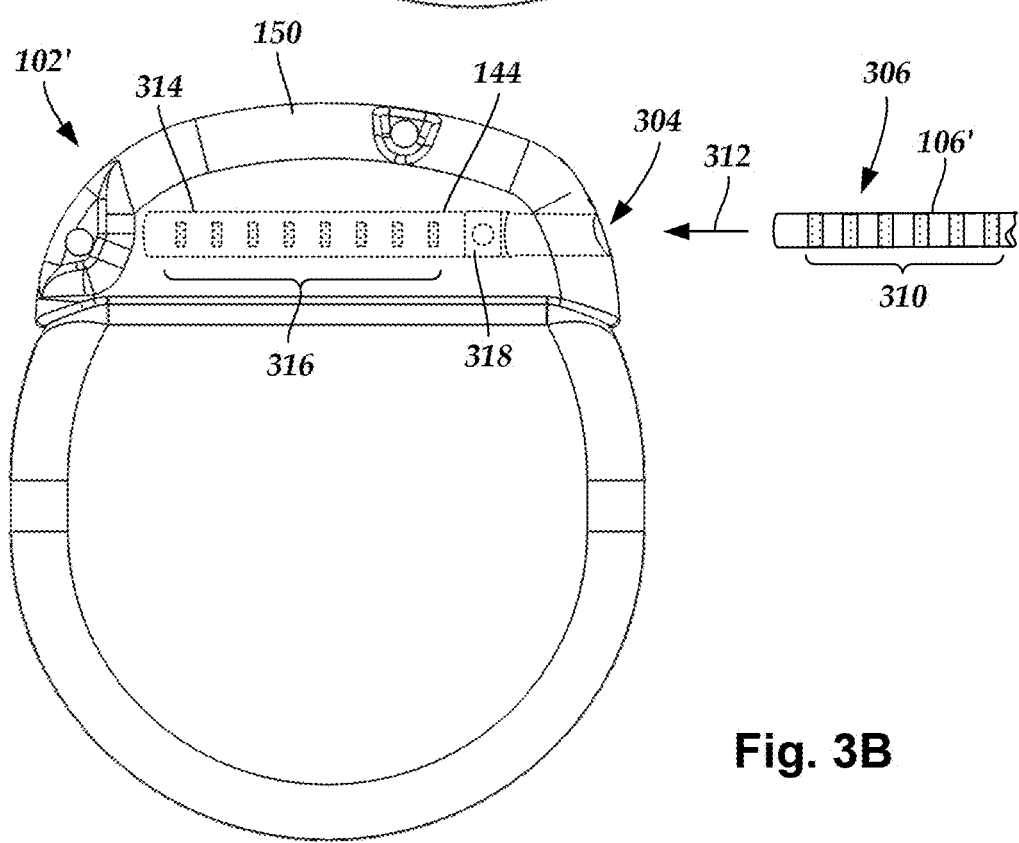
FIG. 3B is a schematic view of one embodiment of a connector assembly disposed in the control module of FIG. 2, the connector assembly configured to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured for insertion to the control module 102. FIG. 3B is a schematic side view of one embodiment of a single connector assembly 144 disposed on the control module 102'. In FIG. 3B, the proximal end 306 of the single lead body 106' is shown configured for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
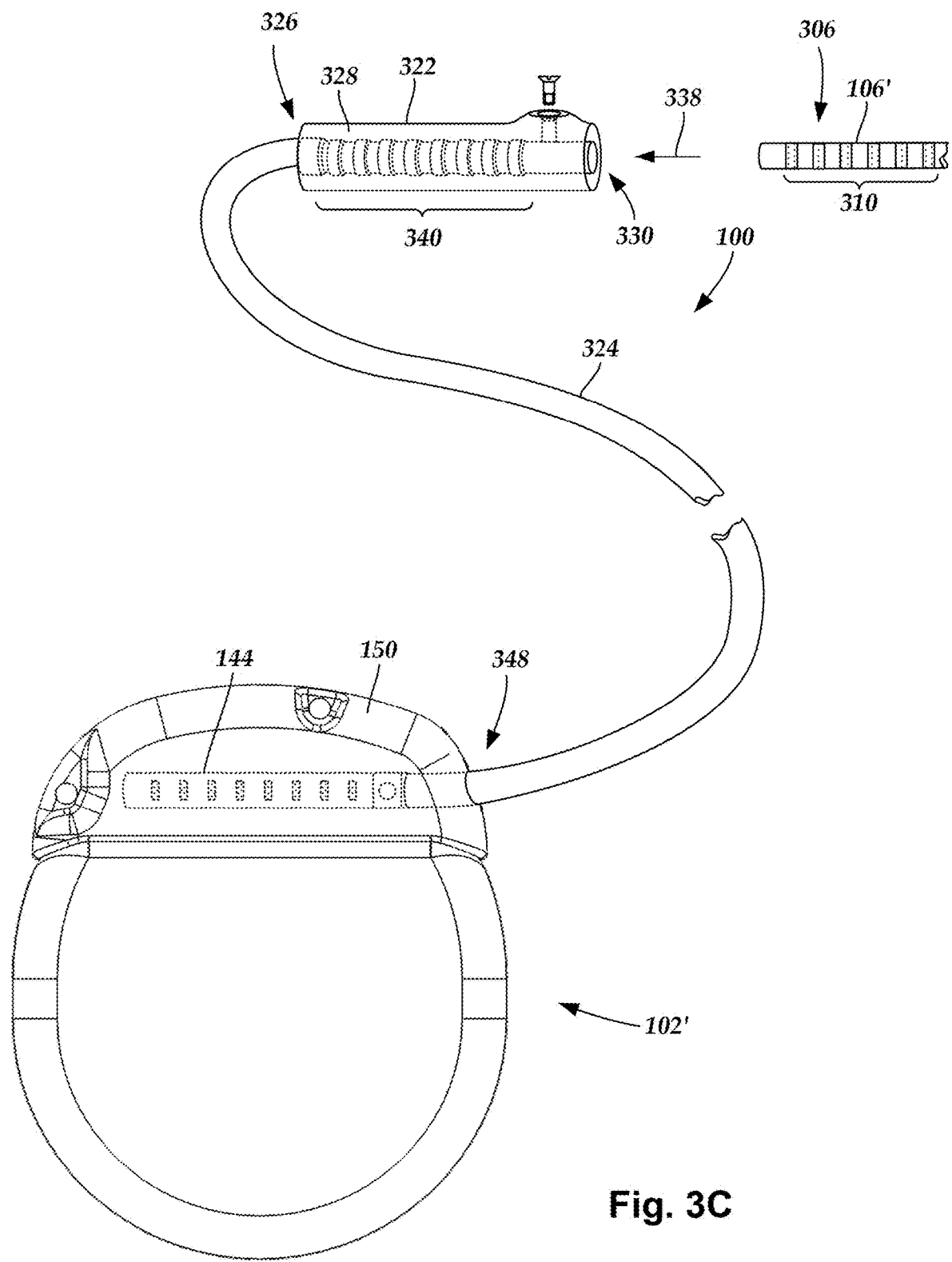
FIG. 3C is a schematic view of one embodiment of a proximal portion of the lead body of FIG. 2, a lead extension, and the control module of FIG. 2, the lead extension configured to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured for insertion into a lead extension connector assembly disposed in another lead extension. In other embodiments (as shown in FIG. 3C), the proximal end 348 of the lead extension 324 is configured for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

It will be understood that the connector assembly described below may be disposed in many different locations including, for example, on lead extensions (see e.g., 322 of FIG. 3C), lead adapters, lead splitters, the connector portion of control modules (see e.g., 144 of FIGS. 1-3B), or the like. In preferred embodiments, the connector assemblies are disposed on the distal ends of lead extensions.

Techniques of connecting, placing and anchoring of the connector assembly can result in the bending and deformation of the connector assembly, which in turn may result in misalignment of the contacts and terminals. Also, bending, and thus misalignment, may occur after implantation, particularly with patient movement.

To reduce such misalignment, a connector assembly can permit a controlled amount of bending and may resist bending or limit bending. By way of example, the connector assembly includes one or more inserts or stiffening elements that operate to resist or limit the amount of bending of the connector assembly in one or more directions.

Figure 4A:
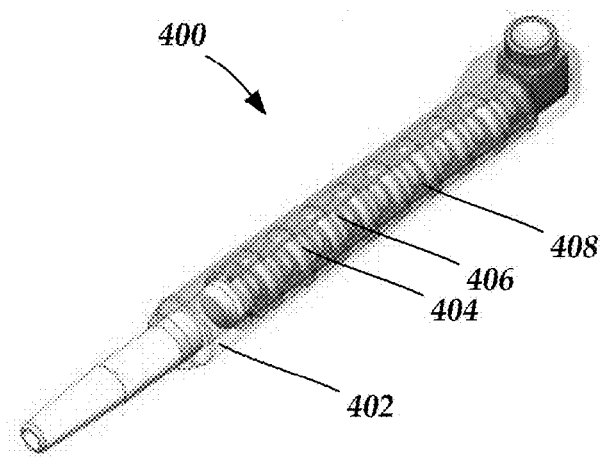
FIG. 4A is a schematic, perspective view of a connector assembly with stiffening elements according to at least some embodiments of the present invention.
Figure 4B:
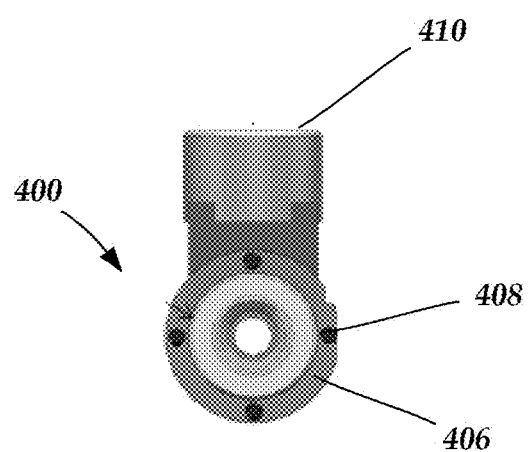
FIG. 4B is a close-up view, cross-sectional view of the connector assembly of FIG. 4A.

FIG. 4A shows a schematic, perspective view of a connector assembly 400 having a connector housing 402 covering a plurality of connector contacts 404 that are separated by spacers 406. Stiffening elements 408 extend through the spacers 406 and will be described below in greater detail. The connector contacts 404 may take the form of conductive spring contacts or any other suitable contact arrangement. FIG. 4B shows a cross-sectional view of the connector assembly 400 of FIG. 4A in which the cross-section is taken near a septum 410. The stiffening elements 408 may advantageously limit an amount of bending deformation of the connector assembly 400 whether during implantation or over its operational life.

Figure 4C:
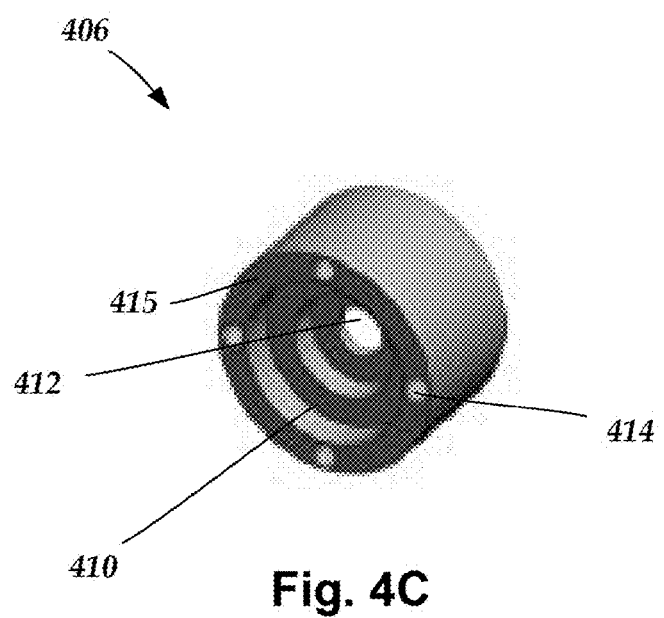
FIG. 4C is a close-up view, perspective view of the connector housing of FIG. 4A showing the apertures for receiving the stiffening elements.
Figure 4D:
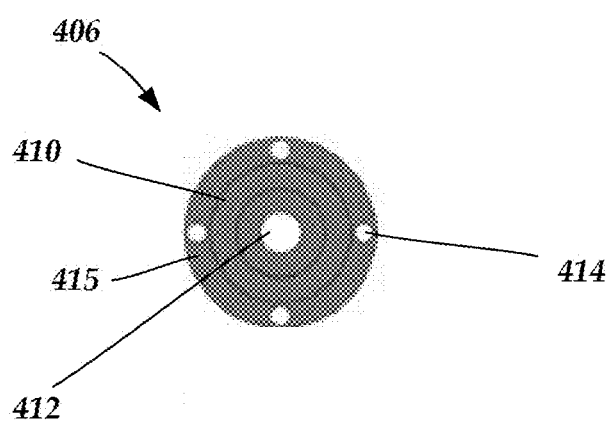
FIG. 4D is a close-up view, cross-sectional view of the connector housing of FIG. 4C.

FIGS. 4C and 4D shows a schematic, close-up views of one of the spacers 406, which optionally includes a recessed region 410 to receive the connector contact 404 (FIG. 4A). A center lumen 412 extends through the spacer 406. The spacer 406 includes a plurality of apertures 414 for receiving the stiffening elements 408 (FIG. 4A). In at least some embodiments, the apertures 414 may run the full length of the connector assembly or just a partial length of the connector assembly. Likewise, the stiffening elements 408 may be as long as the apertures 414 or shorter than the apertures 414. Typically, the stiffening elements 408 extend between, and connect, at least two the spacers 406 and, in at least some embodiments, extend between, and connect, all of the spacers 406 of the connector assembly.

In at least some embodiments, the apertures 414 and stiffening elements 408 are disposed radially outside an outer radius of the connector contacts (as illustrated, for example, in FIGS. 4A and 4B.) For example, the apertures 414 and stiffening elements 408 may be disposed in an outer region 415 of the spacer 406 that extends beyond the outer radius of the connector contacts and, at least in some embodiments, may be partially disposed over one or more connector contacts.

While the illustrated embodiment shows four apertures 414, equally spaced, it is appreciated that the spacer 406 may have a single aperture, two or three apertures, or more than four apertures. The apertures 414 may be circumferentially equidistant from each other or may have a non-uniform circumferential spacing. Similarly, the number of stiffening elements 408 may be equal to the number of apertures 414 or less than the number of apertures 414. Additionally or alternatively, some of the stiffening elements 408 may be stiffer or more rigid than other stiffening elements 408.

The connector contacts 404 are electrically insulated from one another by the non-conductive spacers 406. By way of example, the spacers 406 and the connector housing 402 may be made from a non-conductive, biocompatible material such as, for example, silicone, polyurethane, polyetheretherketone ("PEEK"), epoxy, and the like or combinations thereof. The spacers 408 and housing 402 can be made of the same or different materials.

The connector contacts 404 can be formed using any conductive, biocompatible material. Examples of suitable materials include metals, alloys, conductive polymers, conductive carbon, and the like, as well as combinations thereof. In at least some embodiments, one or more of the contacts are formed from one or more of: platinum, platinum iridium, palladium, palladium rhodium, or titanium. The stiffening elements 408 may be made from a metallic material, such as, but not limited to, the materials used for the contacts, or can be made from a rigid plastic or reinforced composite material. In at least some embodiments, the material of the stiffening elements 408 is stiffer than the material of the connector housing 402. In at least some embodiments, the material of the stiffening elements 408 is stiffer than the material of the spacers 406.

Figure 5:
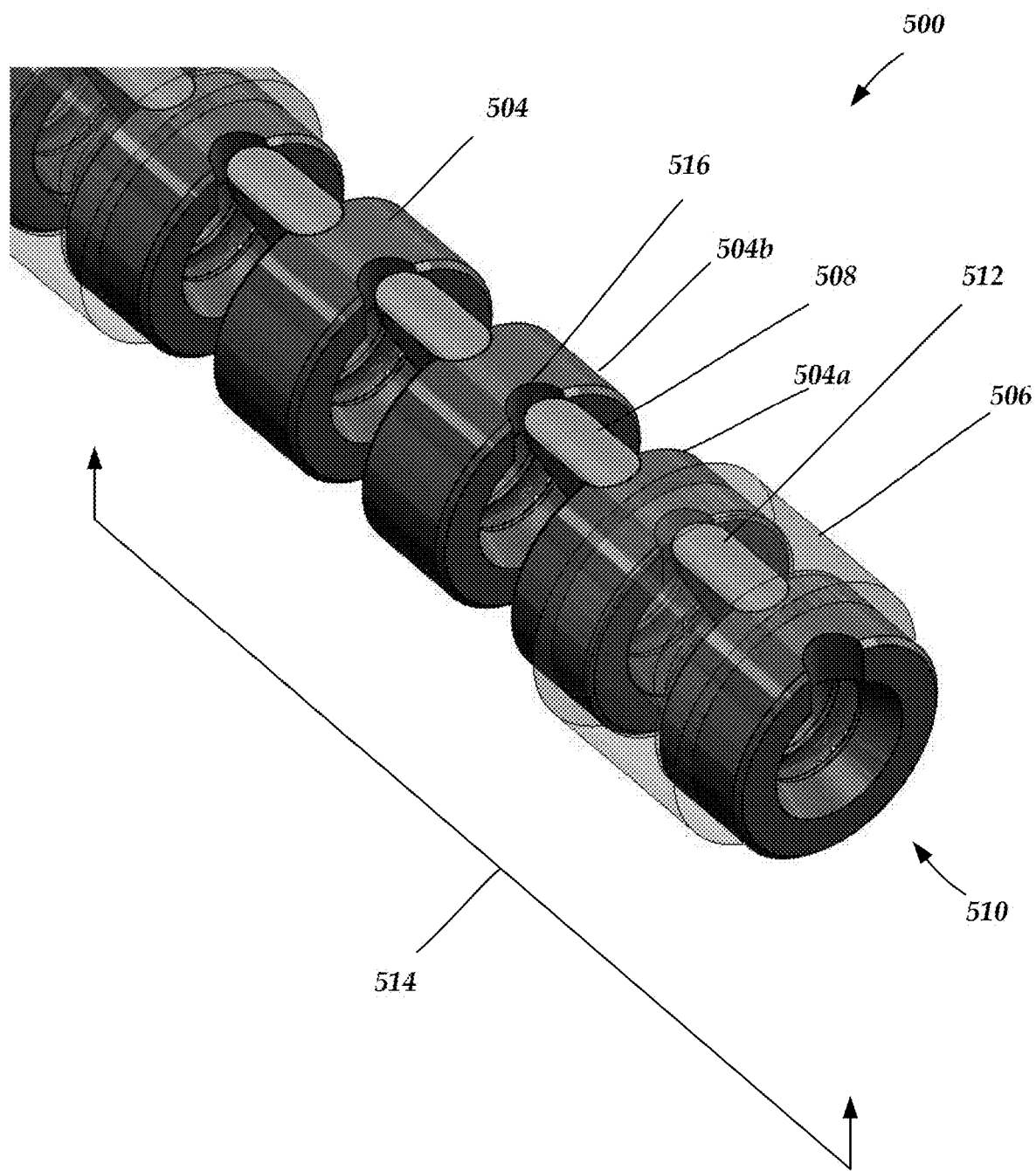
FIG. 5 is a schematic, perspective view of a connector assembly with one set of inserts for limiting bending flexion according to at least some embodiments of the present invention.

FIG. 5 shows a schematic, perspective view of a portion of a connector assembly 500 having a connector housing (not shown for purposes of clarity), connector contacts 504, spacers 506 (only two of which are illustrated for purposes of clarify), and one or more non-conductive inserts 508 that operate as bending limiters as explained below. In the illustrated embodiment, the inserts 508 are arranged along one side of the connector assembly 500 to provide for controlled or allowable bending of the connector assembly 500. The inserts 508 operate as mechanical stops to limit the amount of flexion or distortion of the connector assembly 500 when a bending force is applied in a direction that compresses the insert and adjacent connector contacts 504. In turn, reducing or limiting the amount of bending distortion of the connector assembly may advantageously reduce any misalignment due to bending and thereby improve the electrical communication between the conductive components of the connector assembly, the lead, the lead extension or any other component or device coupled to or received by the connector assembly.

The connector contacts 504 are axially or longitudinally spaced-apart and disposed along a lumen 510 such that the connector contacts 504 are each exposed to the lumen 510. As noted above, the connector contacts 504 are configured for coupling to a proximal end of a lead or lead extension when the proximal end of the lead or lead extension is inserted into the lumen 510. The connector contacts 504 are separated by the spacers 506, which are disposed within the spaces provided between adjacent connector contacts 504. In some embodiments, the spacers 506 are similar to spacers 406 with or without the apertures 414.

At least one of the spacers 506 includes a first region 512, which is the region associated with the respective insert 508. By way of example, a bending force 514 applied to the connector assembly 500 places the first region 512 of the spacer 506 in a compressive state or under a compressive stress. Due to the relative softness and flexibility of the spacers 506, the first region 512 deforms or compresses when under the compressive stress. This compressive deformation, in turn, causes the adjacent connector contacts 504a, 504b to move closer to each other.

To limit or constrain the movement of the adjacent connector contacts 504a, 504b, the non-conductive insert 508 is disposed on or within the first region 512 of the spacer 506. The non-conductive insert 508 has a length that maintains at least a minimum distance between the adjacent connector contacts 504a, 504b when the first region 512 is placed under compressive stress.

In at least some embodiments, the inserts 508 are made from a non-conductive material that is more rigid than the spacer material. For example, the inserts 508 may be made from a rigid plastic material. The inserts 508 may take a variety of shapes and configurations. In the illustrated embodiment, the inserts 508 have an elliptical form, but could be rectangular or some other shape.

It is appreciated that the connector assembly 500 may be bent in a variety of directions. In at least some embodiments, the inserts 508 are longitudinally aligned along one side of the connector assembly to reduce or limit the bending in a plane defined by the aligned inserts 508 (e.g., see schematic bending representation 514). Additionally or alternatively, the number of inserts 508 and their locations may vary depending on an anticipated bending force, weight, size and other factors. By way of a non-limiting example, each spacer 506 may not have an insert disposed on or within it, but instead every other spacer 506 has an insert disposed on or within it. In some embodiments, the spacer 506 has a recess where the insert 508 resides. In other embodiments, the spacer 506 may have an open interior space within which the insert 508 resides and can move. In yet other embodiments, the spacer 506 partially or fully surrounds the insert 508.

In at least some embodiments, the connector contacts 504 can optionally include recesses 516 for receiving the inserts 508 and for limiting the distance that the connector contacts 504 can move when the in-plane bending force 514 is applied to the connector assembly 500. The length of the recesses 516 provides the limiting factor for how far the connector contacts 504 can move toward each other when the connector assembly 500 is bent. The recesses 516 may extend all the way through the wall thickness of the connector contacts 504 or partially through. The recesses 516 have a shape that is complementary to the shape of an end portion of the inserts 508. Referring to the illustrated embodiment, the recesses 516 take the form of half-circular shaped cutouts to receive the elliptically shaped inserts 508. However, it is appreciated that the recesses 516 may take other shapes preferably consistent with the shapes of the inserts 508.

Figure 6:
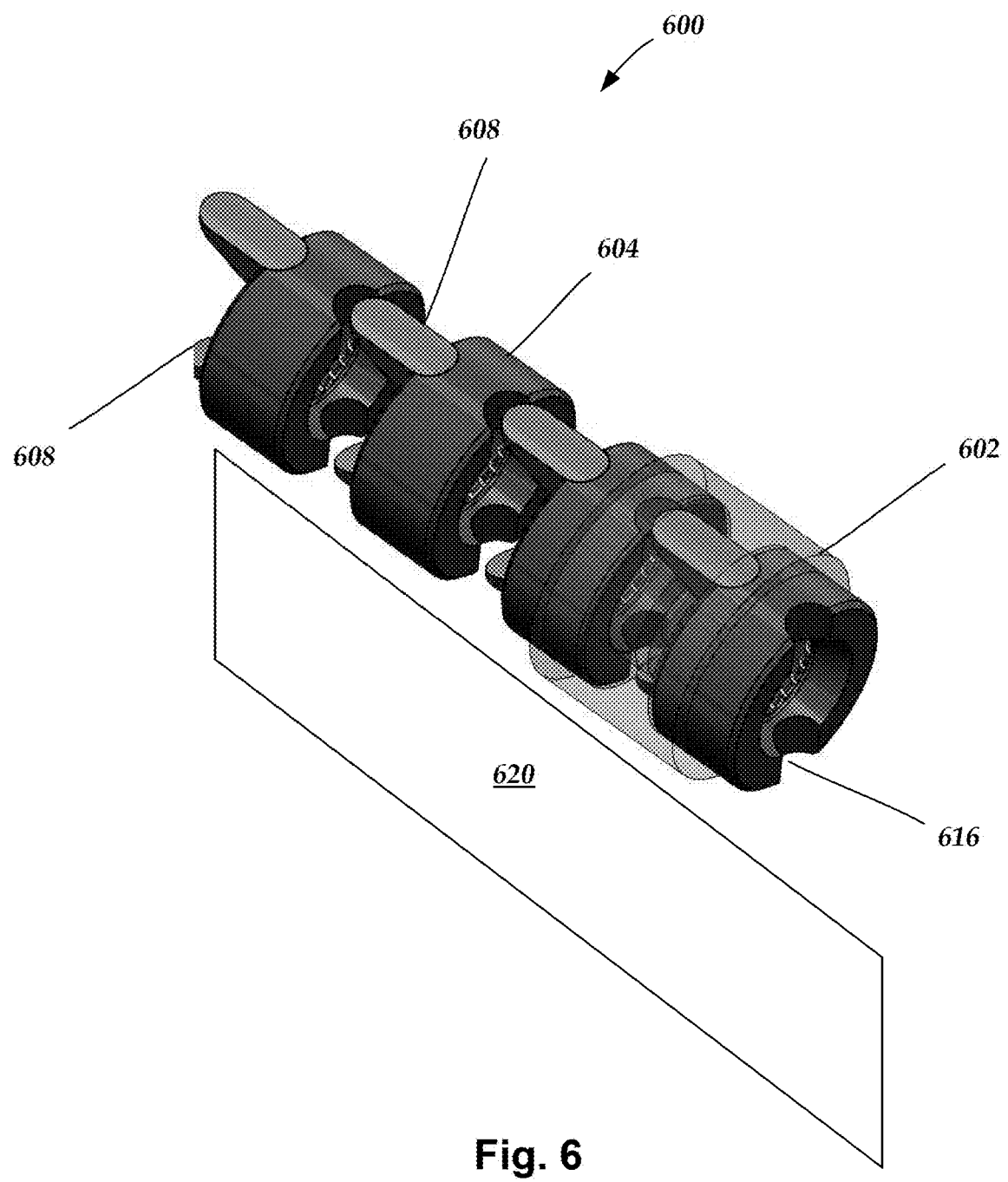
FIG. 6 is a schematic, perspective view of a connector assembly with more than one set of inserts for limiting bending flexion according to at least some embodiments of the present invention.

FIG. 6 shows a schematic, perspective view of another connector assembly 600 having a connector housing (not shown for purposes of clarity), connector contacts 604, spacers 606, and one or more non-conductive inserts 608 that operate as bending limiters. For purposes of brevity, the illustrated connector assembly 600 is structurally and functionally similar to the connector assembly 500 described above except that the inserts 608 are provided on at least two sides (e.g., opposing sides) of the connector assembly 600 to limit bi-directional, in-plane bending as schematically represented by bending plane 620. Optionally, another set or sets of inserts could be provided on other quadrants of the connector assembly 600 to limit bending in a direction that is non-parallel to the bending plane 620. The number of inserts or the number of sets of inserts may be 1, 2, 3, 4 or more. The sets of inserts may be circumferentially equidistant from each other or may be spaced in a non-uniform circumferential manner. For example, there may be four sets of inserts that are arranged at 90 degree intervals around the circumference of the connector assembly.

Figure 7A:
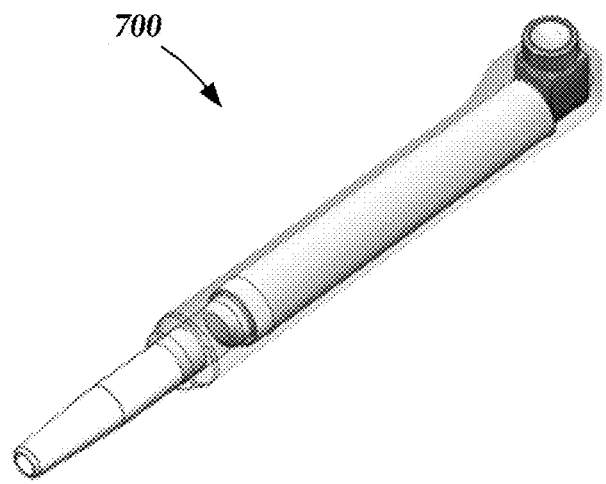
FIG. 7A is a schematic, perspective view of a connector assembly with a stiffening sleeve installed over the connector housing according to at least some embodiments of the present invention.
Figure 7B:
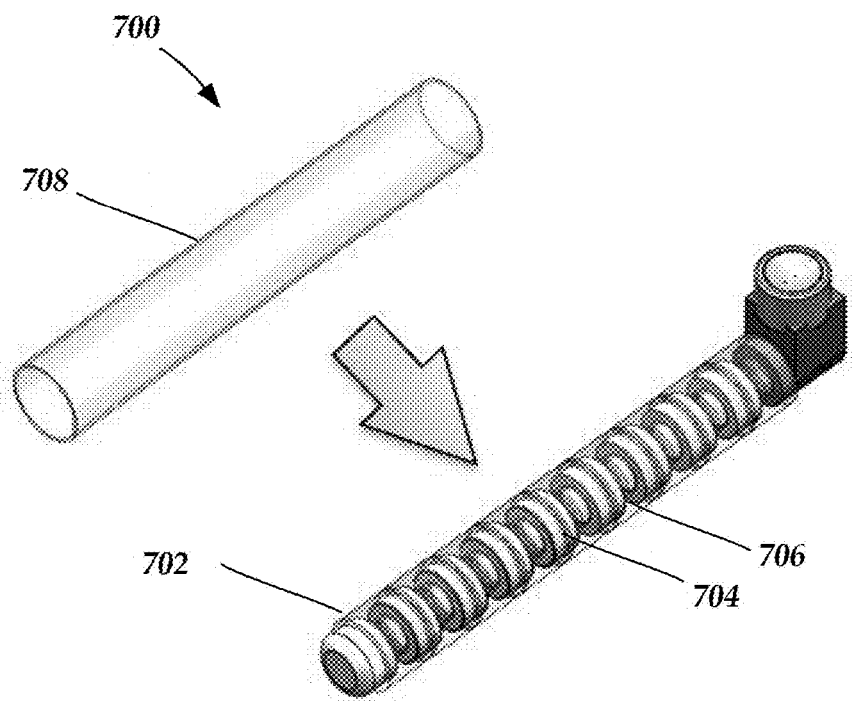
FIG. 7B is a schematic, perspective, exploded view of a connector assembly of FIG. 7A.

FIGS. 7A and 7B show schematic, perspective views of a connector assembly 700 having a connector housing 702 covering a plurality of connector contacts 704 that are separated by spacers 706. In the illustrated embodiment, a stiffening sleeve 708, such as a cylinder or tube, is placed over the connector contacts 704 and spacers 706 and within the connector housing 702.

In at least some embodiments, the stiffening sleeve 708 may take the form of a mesh sleeve that increases the stiffness of the overall connector assembly 700. In other embodiments, the stiffening sleeve may be a solid sleeve. The stiffening sleeve 708 may be made from a rigid material such as a metal or a plastic. In at least one embodiment, the stiffening sleeve 708 is made from a fluorinated ethylene propylene (FEP) material that is installed on the connector housing 702 through a heat shrinking process.

The stiffening sleeve 708 may be installed within the connector housing 702 by a variety of techniques such as, but not limited to, interference fitting, bonding, or press fitting. Additionally or alternatively, the increase of overall bending stiffness provided by the addition of the stiffening sleeve 708 is dependent on a variety of factors that include, but are not limited to, the design of the sleeve (e.g., thickness, length, etc.), the material of the sleeve (e.g., metal or plastic), and the construction of the sleeve (e.g., a tightly wound mesh sleeve as compared to a loosely wound mesh sleeve).

Figure 8:
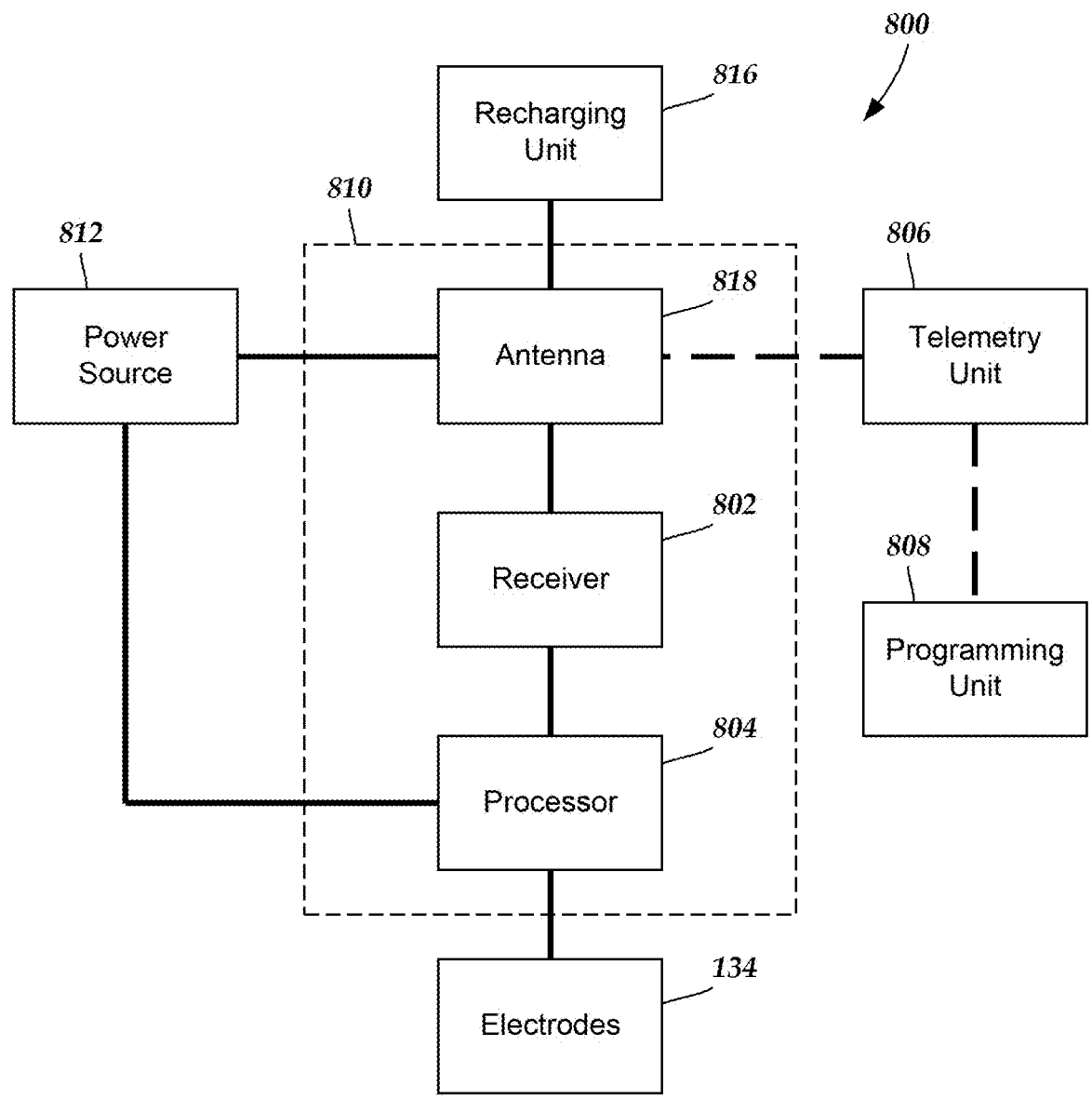
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A connector assembly comprising:
    an elongated connector housing having a first end, a second end, and a length, the connector housing defining a port at the second end of the connector housing, the port configured for receiving a proximal end of a lead or lead extension;
    a lumen that extends from the port along at least a portion of the length of the connector housing;
    a plurality of connector contacts axially spaced-apart and disposed along the lumen such that the connector contacts are each exposed to the lumen, the connector contacts configured for coupling to a proximal end of a lead or lead extension when the proximal end of the lead or lead extension is inserted into the lumen;
    a plurality of non-conductive spacers disposed between adjacent connector contacts, at least one of the plurality of non-conductive spacers comprises a first region; and
    at least one non-conductive first insert disposed on or within the first region between adjacent connector contacts, the at least one non-conductive first insert having a length that permits a limited amount of bending in a first direction parallel to the length of the at least one non-conductive first insert and maintains a minimum distance between the adjacent connector contacts when the first region is placed under a compressive stress during the bending in the first direction,
    wherein, for each of the at least one non-conductive first insert, the adjacent connector contacts each comprise a first insert engagement region which the at least one non-conductive first insert engages during bending in the first direction to maintain the minimum distance, wherein, absent bending, a distance between furthest opposite sides of the first insert engagement regions of the adjacent connector contacts is greater than the length of the at least one non-conductive first insert to permit the limited amount of bending in the first direction.
2. The connector assembly of claim 1, wherein the non-conductive spacers are made from a first material and the at least one non-conductive first insert is made from a second material that is stiffer than the first material.
3. The connector assembly of claim 1, wherein each of the non-conductive spacers comprises the first region, and the at least one non-conductive first insert comprises a plurality of non-conductive first inserts with one of the non-conductive first inserts disposed in the first region of each of the non-conductive spacers.
4. The connector assembly of claim 3, further comprising a plurality of second inserts with a one of the second inserts disposed on or within each of the plurality of non-conductive spacers, the second inserts longitudinally aligned and circumferentially offset with respect to the non-conductive first inserts, the second inserts having a length that permits a limited amount of bending in a second direction parallel to the length of the second inserts and maintains a minimum distance during the bending in the second direction.
5. The connector assembly of claim 4, wherein, for each of the second inserts, the adjacent connector contacts each comprise a second insert engagement region which the second inserts engage during bending in the second direction to maintain the minimum distance, wherein, absent bending in the second direction, a distance between furthest opposite sides of the second insert engagement regions of the adjacent connector contacts is greater than the length of the second inserts to permit the limited amount of bending in the second direction.
6. The connector assembly of claim 1, further comprising at least one non-conductive second insert disposed on or within at least one of the plurality of non-conductive spacers, wherein the at least one non-conductive second insert is circumferentially offset with respect to the at least one non-conductive first insert disposed on or within the first region, the at least one non-conductive second insert having a length that permits a limited amount of bending in a second direction parallel to the length of the at least one non-conductive second insert and maintains a minimum distance during the bending in the second direction.
7. The connector assembly of claim 6, further comprising at least one third and at least one fourth insert disposed on or within at least one of the plurality of non-conductive spacers, wherein the at least one non-conductive first insert disposed on or within the first region and the at least one non-conductive second insert, the at least one third insert, and the at least one fourth insert are circumferentially and equidistantly spaced apart with respect to each other.
8. The connector assembly of claim 7, wherein bending of the connector assembly in a direction different from the first direction causes at least one of the at least one non-conductive second insert, the at least one third insert, or the at least one fourth insert to maintain at least a minimum distance between the adjacent connector contacts.
9. The connector assembly of claim 6, wherein, for each of the at least one non-conductive second insert, the adjacent connector contacts each comprise a second insert engagement region which the at least one non-conductive second insert engages during bending in the second direction to maintain the minimum distance, wherein, absent bending in the second direction, a distance between furthest opposite sides of the second insert engagement regions of the adjacent connector contacts is greater than the length of the at least one non-conductive second insert to permit the limited amount of bending in the second direction.
10. The connector assembly of claim 1, wherein the at least one non-conductive first insert is disposed, at least partially, by a recess formed in a one of the non-conductive spacers.

11. The connector assembly of claim 1, wherein the elongated connector housing is disposed over the connector contacts, the non-conductive spacers and the at least one non-conductive first insert.

12. A lead assembly comprising:
   a lead; and
   a lead extension that contains the connector assembly of claim 1, the lead extension having a proximal end and a distal end, wherein the proximal end of the lead extension includes a plurality of terminals electrically insulated from one another.

13. An electrical stimulating system comprising:
   the lead assembly of claim 12; and
   a control module coupleable to the lead assembly, the control module comprising
      a housing, and
      an electronic subassembly disposed in the housing.

14. The connector assembly of claim 1, wherein the first insert engagement region of each of the adjacent connector contacts forms a recess in the connector contact.

15. The connector assembly of claim 14, wherein the at least one non-conductive first insert is disposed in the recess of the first engagement region of a one of the adjacent connector contacts.

16. The connector assembly of claim 15, wherein, when bending in the first direction, the at least one non-conductive first insert is disposed in the recess of the first engagement region of two of the adjacent connector contacts.

17. The connector assembly of claim 15, wherein each of the at least one non-conductive first insert has an elliptical shape.

18. The connector assembly of claim 17, wherein each of the recesses takes a form of a half-circular shaped cutout.

19. The connector assembly of claim 1, wherein each of the at least one non-conductive first insert has an elliptical or rectangular shape.

20. The connector assembly of claim 1, wherein only every other one of the non-conductive spacers has one of the at least one non-conductive first inserts disposed on or in the non-conductive spacer.

\* \* \* \* \*